(12) United States Patent
Kessler (10) Patent No.: US 7,938,118 B2
(45) Date of Patent: May 10, 2011

(54) COMBINATION LARYNGEAL MASK AIRWAY WITH DUAL BLOCKING AND FLUID REMOVAL FEATURES AND METHOD

(76) Inventor: Joel D. Kessler, University Heights, OH (US)

(*) Notice: Subject to any disclaimer, the term of this patent is extended or adjusted under 35 U.S.C. 154(b) by 1044 days.

(21) Appl. No.: 11/694,111

(22) Filed: Mar. 30, 2007

(65) Prior Publication Data
US 2007/0240722 A1 Oct. 18, 2007

Related U.S. Application Data

(60) Provisional application No. 60/789,975, filed on Apr. 6, 2006.

(51) Int. Cl.
*A61M 11/00* (2006.01)
(52) U.S. Cl. ......... 128/207.15; 128/207.14; 128/200.26; 604/96.01
(58) Field of Classification Search ............. 128/207.15, 128/207.14, 200.26; 604/96.01
See application file for complete search history.

(56) References Cited

U.S. PATENT DOCUMENTS

| | | |
|---|---|---|
| 4,688,568 A | 8/1987 | Frass et al. |
| 5,303,697 A | 4/1994 | Brain |
| 5,392,774 A | 2/1995 | Sato |
| 5,513,627 A | 5/1996 | Flam |
| 5,623,921 A | 4/1997 | Kinsinger et al. |
| 6,070,581 A | 6/2000 | Augustine et al. |
| 6,079,409 A * | 6/2000 | Brain ................ 128/200.26 |
| 6,439,232 B1 * | 8/2002 | Brain ................ 128/207.15 |
| 6,634,354 B2 | 10/2003 | Christopher |

OTHER PUBLICATIONS

The Laryngeal Mask Company Limited, LMA-ProSeal Instruction Manual, 2002.
Catalog Sheets from LMA-ProSeal, 2 pages, indicates sizes & catalog numbers, new features and design of product.

* cited by examiner

*Primary Examiner* — Steven O Douglas
(74) *Attorney, Agent, or Firm* — Renner, Otto, Boisselle & Sklar, LLP (57) ABSTRACT

The present invention relates generally to the field of laryngeal mask airway devices. The invention provides for dual passageways in a laryngeal mask which permits a physician to effectively isolate the trachea from the esophagus. In one embodiment, the physician separately inserts an instrumentality (e.g., an endotracheal tube) into a patient's esophagus in order to isolate the stomach from the lungs, respectively. In another embodiment, the physician inserts an instrumentality (e.g., an endotracheal tube) into the trachea and inserts another instrumentality (e.g., a drainage tube) in the second passageway within the laryngeal mask in order to remove particles or fluids contained in the laryngeal mask that may cause problems if allowed to flow through the patient's trachea to the lungs.

16 Claims, 9 Drawing Sheets

COMBINATION LARYNGEAL MASK AIRWAY WITH DUAL BLOCKING AND FLUID REMOVAL FEATURES AND METHOD

CROSS-REFERENCE TO RELATED APPLICATION

This application claims the benefit of U.S. Provisional Patent Application Ser. No. 60/789,975, filed Apr. 6, 2006, the entire disclosure of which is hereby incorporated by reference.

BACKGROUND

1. Technical Field

The present invention relates generally to the field of anesthesiology and to patient ventilating and anesthetizing and, more particularly, to a combination laryngeal mask airway with dual blocking and fluid removal features and method to ventilate a patient while isolating the trachea and the esophagus from each other.

2. Description of the Related Art

Airway devices are widely used in hospital surgical environments to provide respiratory assistance and to ventilate patents during medical procedures. Reference to ventilating includes providing breathable air or oxygen, for example, and removing gas, etc., e.g., exhalant exhaled by a patient, and providing anesthesia and/or other materials to and/or from the lungs of a patient. Ventilating also has the usual meaning as used in the field of medicine. The various gases, e.g., oxygen, air, anesthesia, etc., alone or in combination sometimes are referred to below collectively as gas mix.

While there are a multitude of airway devices currently on the market, one popular airway device is an endotracheal tube and another is a laryngeal mask airway (sometimes referred to in abbreviation as LMA). While the use of these devices is widespread, there are disadvantages associated with each of these devices.

As one example, endotracheal tubes are used to ventilate patients requiring anesthesia and/or respiratory assistance. An example of a conventional endotracheal tube is a plastic tube, which is inserted into a patient's mouth, is passed down the trachea through the vocal cords and is lodged in the trachea proximal (or above) to the lungs. The endotracheal tube may have a cuff or balloon portion surrounding the circumference of the endotracheal tube near the distal end that rests in the patient's trachea. After the endotracheal tube has been inserted properly, the cuff may be inflated to seal against walls of the trachea. Once sealed, positive pressure ventilation may be used to provide respiratory assistance and, if desired, anesthesia or other gas, gas mix, etc., to the patient though the endotracheal tube via a ventilator. The cuff provides a seal that tends to block liquids and solids from passing along the outside of the endotracheal tube between the tube and trachea walls and entering the patient's lungs.

While endotracheal tubes are ubiquitous in modern medicine, there are problems associated with the insertion of endotracheal tubes in patients. For example, there may be difficulty inserting the endotracheal tube into the proper position within the patient's trachea. A physician inserting the endotracheal tube may have difficulty viewing the trachea and there exists a possibility of inserting the endotracheal tube into the patient's esophagus, which leads to the patient's stomach rather than to the patient's lungs. If the tube is misdirected to the stomach, the lungs may not receive the proper air/oxygen mix. Additionally, the stomach may become filled with air possibly causing the patient to regurgitate, and the regurgitated material from the stomach may back flow and get into the patient's lungs. Another disadvantage of using an endotracheal tube is the invasive nature of intubation.

A laryngeal mask airway (LMA) overcomes many disadvantages associated with endotracheal tubes. An example of an LMA is disclosed in U.S. Pat. No. 6,634,354, issued Oct. 21, 2003 to Christopher, which is incorporated in its entirety by this reference. That LMA includes a hollow tube (sometimes referred to as a tubular guide, tube or guide) and a laryngeal mask. The laryngeal mask of the LMA is intended to fit in the mouth of a patient and to cover the two openings leading, respectively, to the esophagus and to the trachea, on the one hand, blocking the fluid path to and from the esophagus and stomach and, on the other hand, providing a fluid path to the trachea and lungs for ventilating the patient. The laryngeal mask may be positioned without requiring the physician to view the airway directly. The laryngeal mask has an inflatable cuff or rim area. Once the laryngeal mask is placed into the patient's mouth, the cuff can be inflated to seal against the walls of the inside of the mouth and, if positioned properly, to block flow to and from the esophagus. A rubber, plastic or like flexible, somewhat membranous support material extends from the cuff to form a recessed area, e.g., a space or volume, into which gas mix can be pumped through the tube or other instrumentality of the LMA to provide the requisite air and/or anesthesia to the patient. The tube is of relatively large diameter, as compared to the usually relatively narrower diameter passage of a conventional endotracheal tube, and such relatively large diameter facilitates gas mix and exhalant flow with relatively minimal interference, pressure drop, etc. The support material supports the cuff from the tube. Thus, the LMA can be used to supply gas mix to the recessed area and from there to the trachea. An advantage of an LMA is that the patient ordinarily does not have to be intubated with an endotracheal tube. If the LMA is not fully blocking flow to and from the esophagus, the gas mix primarily will flow to the lungs via the trachea because the trachea-lungs flow path generally has less resistance than the flow path from the esophagus to the stomach, and provided the pressure is not too great, the vast majority of the gas mix will flow into the lungs, and the stomach will not fill with the gas mix.

A drawback with the LMA is that the device cannot be used on all patients. For example, the device cannot be used on patients that are at risk for vomiting because if the laryngeal mask is not in the proper position, it does not fully isolate the airway to the trachea from the passageway to the esophagus. Thus, if the patient vomits during a medical procedure in which the LMA is used, the expelled fluid or solids could potentially flow from the esophagus to the trachea and enter the patient's lungs. An LMA ordinarily would not be used for patients that have eaten in the six hours prior to surgery, pregnant women, and trauma victims.

Thus, there is a need in the art to address the above mentioned and possibly other deficiencies and inadequacies of the prior art.

SUMMARY OF THE INVENTION

The present invention relates to a laryngeal mask airway and method for isolating a patient's trachea and esophagus during a medical procedure in which a laryngeal mask is used to supply ventilation or respiratory assistance to the patient.

An aspect of the invention relates to a laryngeal mask airway wherein the esophagus may be intubated for isolation from the trachea, drainage maybe provided for fluids from the esophagus, and a relatively unimpeded or broad path is provided for air, anesthesia, etc. to the trachea of a patient.

One aspect of the present invention relates to a laryngeal mask airway device including: a tubular guide including a distal portion and a proximal portion; a laryngeal mask attached to the distal portion of the tubular guide, wherein the laryngeal mask includes a recessed proximal portion and a distal portion; a first passageway extending from the proximal portion of the tubular guide to the recessed proximal portion of the laryngeal mask; and a second passageway extending through a distal portion of the laryngeal mask.

Another aspect of the present invention relates to a laryngeal mask airway device including: a tubular guide including a distal portion and a proximal portion; a laryngeal mask attached to the distal portion of the tubular guide, wherein the laryngeal mask further includes a support member; a first passageway extending from the proximal portion of the tubular guide to a position within the laryngeal mask located above the support member; and a second passageway extending generally along the tubular guide and extending through a distal portion of the laryngeal mask.

Another aspect of the present invention relates to a method for using a laryngeal mask airway device, the method including: inserting a portion of a laryngeal mask airway device including a laryngeal mask and a portion of a tubular guide into an associated patient's mouth; inflating the laryngeal mask; supplying air to the patient after insertion of the laryngeal mask airway device; inserting a first instrumentality through a first passageway of the laryngeal mask airway device into the patient's esophagus; inflating a cuff associated with the first instrumentality to effectively block the patient's esophagus; and providing a gas to the associated patient through a second passageway of the laryngeal mask airway device into the patient's trachea.

Another aspect of the present invention relates to a method for using a laryngeal mask airway device, the method including: inserting a portion of a laryngeal mask airway device including a laryngeal mask and a portion of a tubular guide into an associated patient's mouth; inflating the laryngeal mask; supplying air to the patient after insertion of the laryngeal mask airway device; inserting a first instrumentality through a first passageway of the laryngeal mask airway device into the patient's trachea; inflating a cuff associated with the first instrumentality to effectively seal the patient's trachea; providing a gas to the patient through the first instrumentality; inserting a second instrumentality through a second passageway of the laryngeal mask into the laryngeal mask; and removing at least one of fluids or particles released from the patient's stomach into the laryngeal mask through the second instrumentality.

These and other systems, methods, features, and advantages of the present invention will be or become apparent to one with ordinary skill in the art upon examination of the following drawings and detailed description. It is intended that all such additional systems, methods, features, and advantages be included within this description, be within the scope of the present invention, and be protected by the accompanying claims.

In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

It should be emphasized that the term "comprise/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Likewise, elements and features depicted in one drawing may be combined with elements and features depicted in additional drawings. Moreover, in the drawings, like reference numerals designate corresponding parts throughout the several views, and primed reference numerals represent parts that are similar to those parts designated by the same unprimed reference numeral.

FIG. 3A is a side elevation view partly in section and perspective of a laryngeal mask airway in accordance with an embodiment of the present invention with the laryngeal mask inflated and a passageway extending through part of the laryngeal mask for placement and holding of an endotracheal tube or the like;

FIG. 3B is a top plan view partly in section of the distal portion of the laryngeal mask airway of FIG. 3A.

FIG. 3C is an enlarged side elevation view partly in section of part of the laryngeal mask and passageway shown in FIGS. 3A and 3B;

BRIEF DESCRIPTION OF PRIOR ART

Figures 1A, 1B:
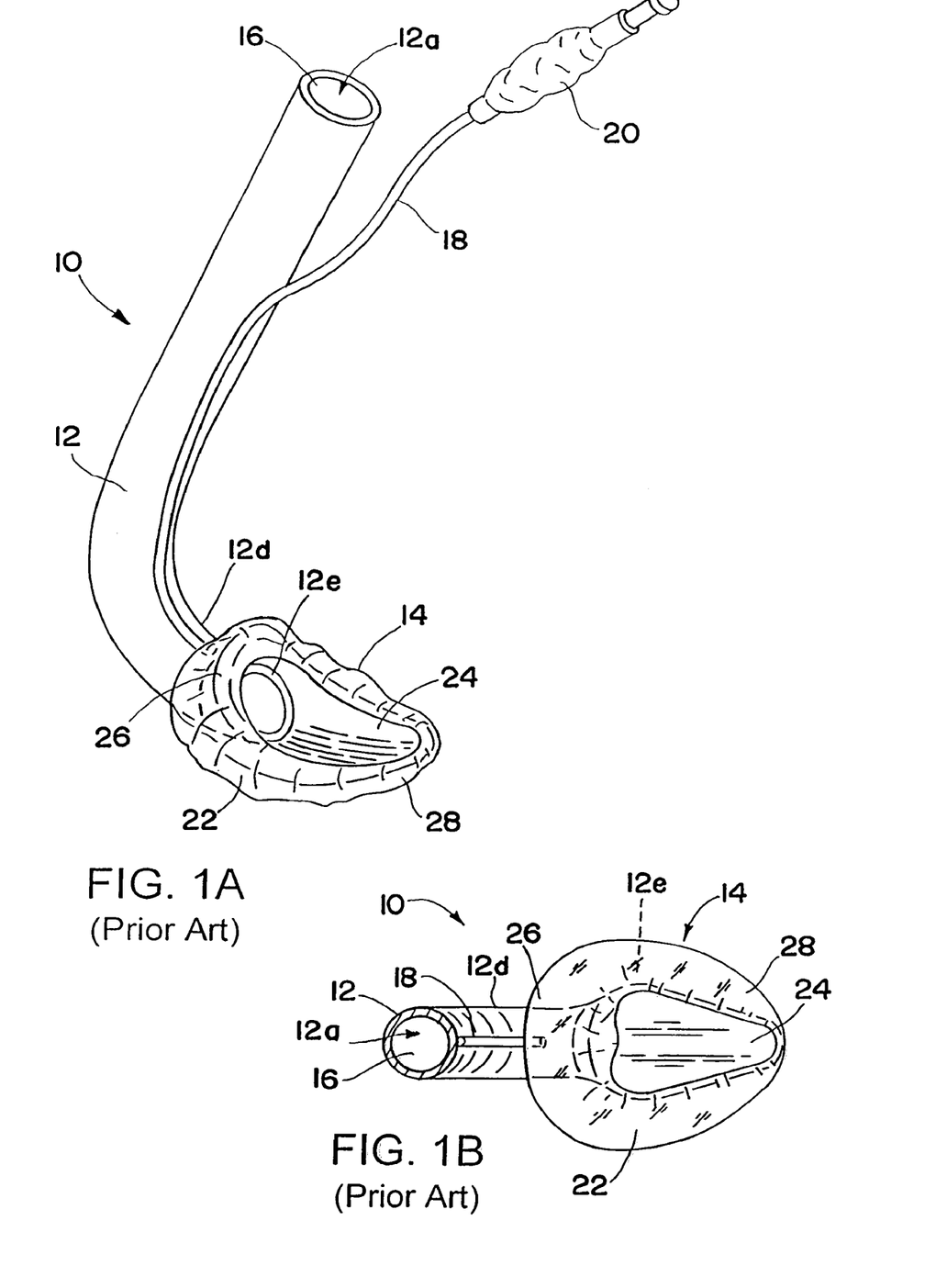
FIG. 1A is a front perspective view of an exemplary prior art laryngeal mask airway.
FIG. 1B is a cross-sectional view of the distal portion of the exemplary laryngeal mask airway of FIG. 1A.
Figure 2:
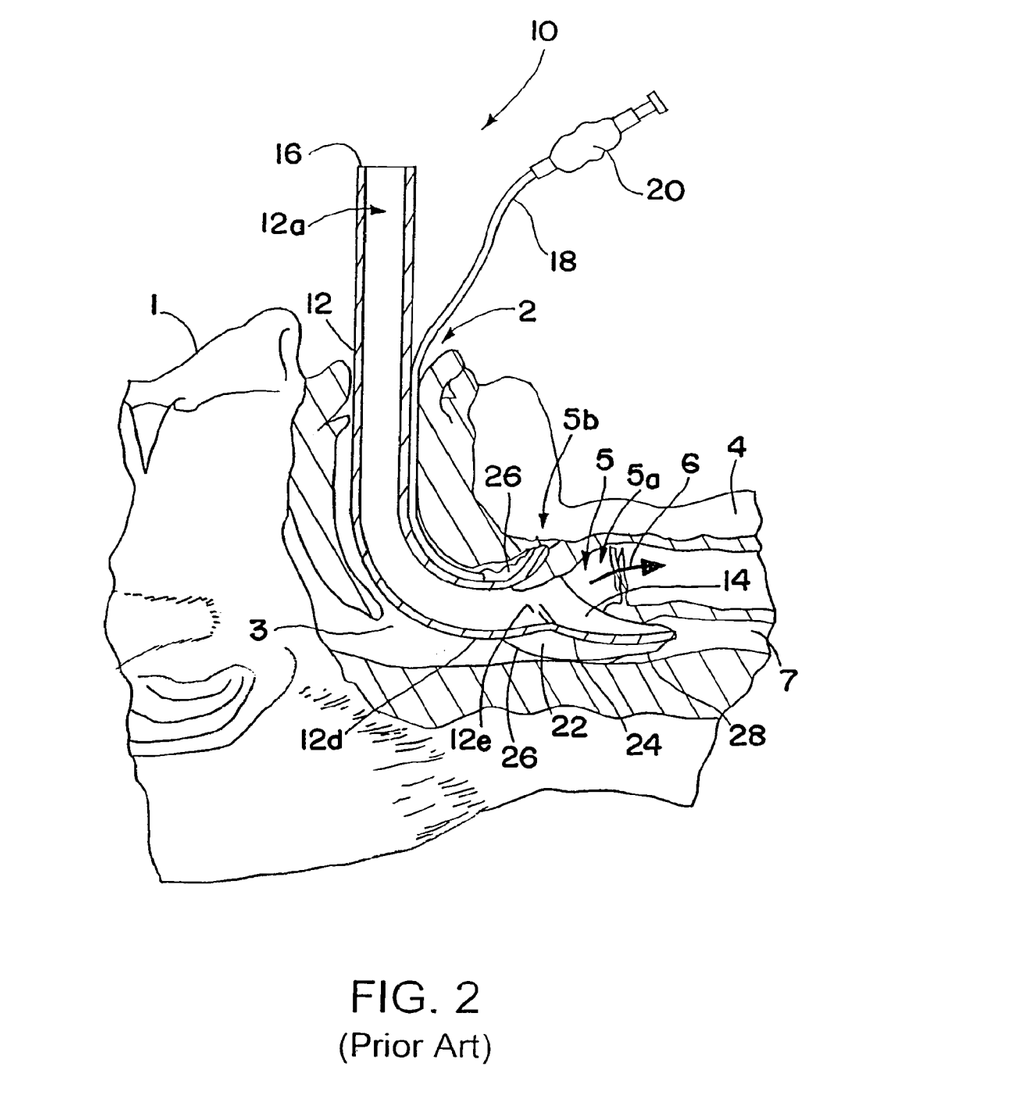
FIG. 2 is a cross-sectional view of the exemplary prior art laryngeal mask airway of FIGS. 1A and 1B and the patient's airway after the laryngeal mask has been inserted and inflated.
Figures 3A, 3B, 3C:
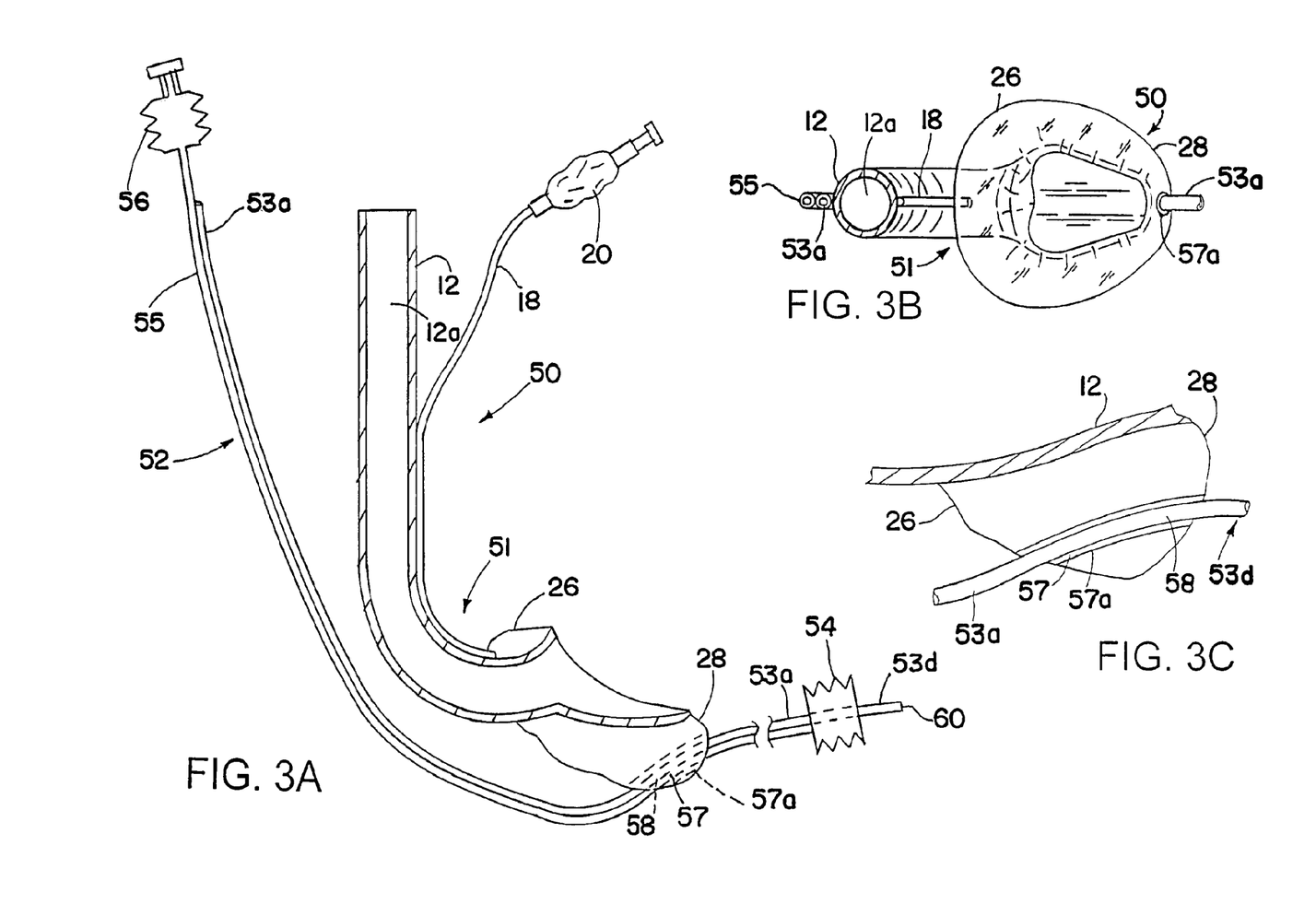

FIGS. 1A, 1B, and 2

The following description is exemplary in nature and is not way intended to limit the scope of the invention as defined by the claims appended hereto. An exemplary laryngeal mask is described in U.S. Pat. No. 6,634,354 to Christopher, which is incorporated by reference as if fully rewritten herein.

In FIGS. 1A. 1B and 2 of the drawings, for example, a patient 1 is shown schematically with the mouth 2 in cross section and open and leading to the back of the throat 3 (sometimes the mouth and/or throat are referred to as the oral cavity of the patient) and from there (i) to the trachea 4 via the laryngeal inlet 5, which provides an airway 6 that leads to the lungs, and (ii) to the esophagus 7, which leads to the stomach; and exemplary laryngeal mask airway (LMA) 10 of the type generally described in the Christopher patent is in the patient. The LMA 10 includes a tubular guide 12, e.g., a hollow tube, sometimes referred to below as a tube or guide, and a laryngeal mask 14 surrounding the distal end 12d of the tubular guide 12. When in use, the proximal end 16 of the tubular guide 12 remains outside of the patient's mouth and, therefore, is accessible to the healthcare provider, e.g., physician, nurse or other individual. The proximal end 16 of the tubular guide 12 may be conveniently of size and shape to secure a variety of attachments to the tubular guide 12 (e.g., a syringe, an endoscope probe, an endotracheal tube, a gas mix supply connection to receive a gas mix for ventilating, anesthetizing, etc., a patient, a drainage tube, etc.). The laryngeal mask airway 10 further includes an inflation tube 18 and an air valve 20 for inflating and deflating an inflatable member 22, e.g., a cuff, of the laryngeal mask 14. In addition, the laryngeal mask airway 10, includes a central support member 24, e.g., a flexible and possibly somewhat elastic or yielding membranous material, as was mentioned above, which generally provides support for the laryngeal mask 14 including the cuff 22 and support member 24 from the tube 12.

Typically, the size and shape of the tubular guide 12 are selected so that the distal portion 12d can be readily inserted into a patient's mouth and upper airway with the laryngeal mask 14 substantially sealing the laryngeal inlet 5 of the patient 1. The tubular guide 12 is generally a J-shape to follow the profile of a typical patient's airway through the mouth, over the tongue, and into the laryngopharynx region of the patient just above the opening 5a to the larynx. The guide 12 is shaped to prevent the patient's tongue and collapsible pharynx from obstructing access to the trachea. The guide 12 further defines a passageway or channel 12a for ventilating a patient, e.g., to direct relatively unimpeded flow of gas mix to the lungs and exhalant from the lungs. The size of the passageway 12a may be suitable for possible later insertion of a tube or other suitable instrumentality. (e.g., endotracheal tube, endoscope, drainage tube, etc.) while still providing space for ventilating the patient. Placing additional tubes or other instrumentalities in the passageway 12a of the tubular guide 12, though, may impede flow for ventilating purpose.

The guide 12 may be made, for example, of plastic with sufficient strength and rigidity to keep the patient's teeth apart and to prevent the patient from biting down and collapsing the guide 12. The guide 12 may be made of other suitable material. The guide 12 is sized to accommodate a wide range of patient sizes and conditions. The distal opening 12e of the guide 12 is beveled to substantially match the angle of the patient's laryngeal inlet after insertion of the laryngeal mask airway 10 into the patient's airway.

Referring to FIG. 1B, a top view of the laryngeal mask 14 of the LMA 10 is illustrated. The laryngeal mask 14 includes an upper portion 26, a lower portion 28 and the central support member 24. The central support member 24 extends outward from the guide 12 to the inflatable member 22 (cuff). The laryngeal mask 14 may be made, for example, of a soft, flexible material (e.g., a polymer or rubber) to enable the laryngeal mask 14 to be advanced into position without injury to the patient and to create, when the cuff is inflated, a substantially air-tight seal about the patient's laryngeal inlet, as is shown in FIG. 2. The degree of inflation of the laryngeal mask 14 member 22 can be adjusted via the inflation tube 18 and air valve 20.

In the ideal use, the laryngeal mask 14 and its support member 22 are positioned in the patient so that the lower portion 28 of the laryngeal mask 14 substantially blocks the esophagus 7 to minimize the risk of regurgitation of stomach contents and the passage of air into the stomach. The upper portion 26 of the laryngeal mask 14 guides the distal end 12d of the guide 12 into alignment using the laryngeal inlet 5 of the patient 1 as a guide to insert along the patient's airway, which is partially represented by the arrow 6.

As is shown in FIGS. 1A and 2, the laryngeal mask 14 may be boot-shape when inflated. The lower portion 28 of the laryngeal mask 14 forms the toe of the boot, which is designed to block the esophagus. The lower portion 28 of the laryngeal mask 14 also helps to align the distal opening 12e of the guide 12 with the patient's laryngeal inlet 5. Once inserted, the inflatable member 22 (cuff) of the laryngeal mask 14 is inflated through the inflation tube 18 so that the upper portion 26 of the laryngeal mask 14 substantially fills the patient's laryngopharynx 5b at the level of the laryngeal inlet 5, as is shown in FIG. 2. The upper portion 26 of the laryngeal mask 14 surrounds the laryngeal inlet 5 so that the distal opening 12e of the guide 12 is substantially sealed in fluid communication with the laryngeal inlet, e.g., pressing against walls of the oral cavity portions of the patient. Thus, substantially all of the gas inhaled or exhaled by the patient is intended to pass through the guide 12.

While the conventional laryngeal mask 14 of the LMA 10 is designed to substantially block the esophagus and to minimize the risk of regurgitation of stomach contents into the patient's lungs, the laryngeal mask 14 may not completely isolate the esophagus from the trachea, especially if the LMA 10 is not properly positioned in the patient, and the problems discussed above limit the number and types of procedures in which the conventional laryngeal airway 10 may be used.

DESCRIPTION OF THE INVENTION

Referring to FIGS. 3-9, a laryngeal mask airway 50 (LMA) in accordance with embodiments of the present invention is illustrated. The LMA 50 includes two fluid conducting portions 51 and 52, which may be cooperative as is described below and which also may provide independent flow paths, passageways or the like, as also is described below. In a sense the two fluid conducting portions 51, 52 of the LMA 50 complement each other; the portion 51 is similar to the LMA 10 (described above) and the portion 52 is similar to an endotracheal tube. The portion 52 may be an endotracheal tube 53a, as is shown in FIG. 4A. Alternatively, the portion 52 may be a tube or sleeve 53b through which an endotracheal tube 53a may be inserted, e.g., as is illustrated in FIG. 4B, the sleeve facilitating such insertion. It will be appreciated that some other instrumentality may be the same as or similar to tubes 53a, 53b in form and function.

Figures 4A, 4B:
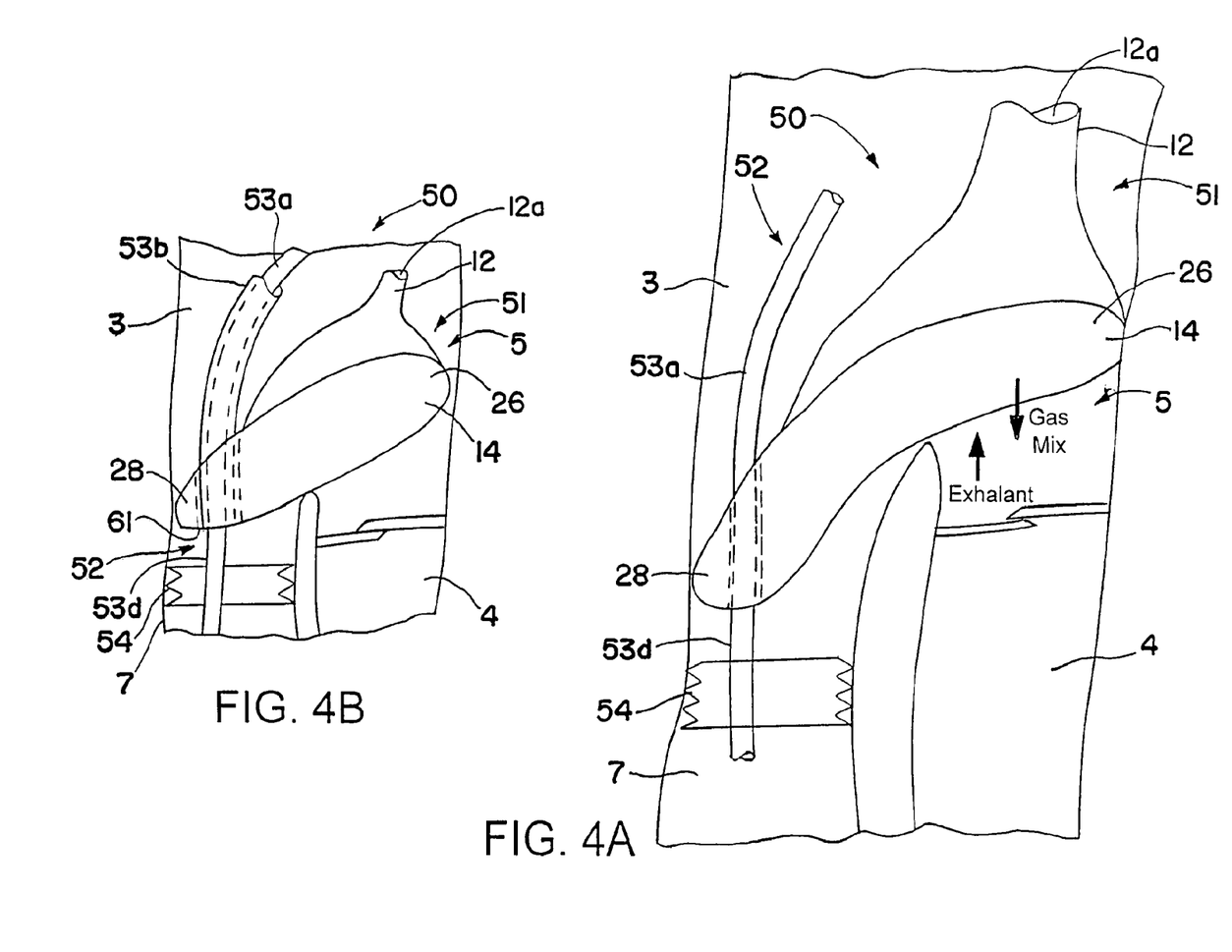
FIGS. 4A and 4b are schematic side elevation views showing respective embodiments of laryngeal mask airways as embodiments of the invention in use in the oral cavity of a patient.

As is illustrated schematically in FIGS. 4A and 4B, in using the LMA 50 it is preferred that the endotracheal tube portion 52 would have its distal end 52d inserted into the esophagus 7 of a patient 1; and it is preferred that the fluid conducting portion 51 would fit the patient such that the distal end 28 of the laryngeal mask 14 thereof would block fluid to and from the esophagus 7 of the patient. At least in part, the complementary relation of the portions 51, 52, as is described below, in a sense is as respective backups or supplements for each other. For example, the endotracheal tube 53a can be positioned in the esophagus to block fluid flow to and from the esophagus except for flow through the tube 53a; and the laryngeal mask 14 of the portion 51 could be positioned also to block fluid flow to and from the esophagus, e.g., generally as is illustrated in FIGS. 2, 4A and 4B. In such case ventilating of the patient can be carried out via the relatively large tube 12 of the portion 51 and laryngeal mask 14 and, if necessary, fluid or other waste can be withdrawn from the stomach and esophagus via the endotracheal tube 53a. Positioning of the endotracheal tube in expanded relation of its sealing balloon 54 in the esophagus and the further positioning of a portion of the laryngeal mask 14 in the entrance to the esophagus provide added protection against fluid or other waste from the esophagus and stomach from reaching the trachea and lungs. Also, such use of the parts of the LMA 50 avoids the need for intubation of the patient, i.e., inserting of the endotracheal tube 53a into the trachea.

Turning to FIGS. 3A, 3B, 3C, 4A and 4B, the LMA 50 includes the first fluid conducting portion 51, which includes a tube 12 and a laryngeal mask 14. The LMA 50 also includes the second fluid conducting portion 52, which includes an elongate hollow endotracheal tube 53a that has an expandable sealing balloon 54 at the distal end 53d, e.g., as are similar to a conventional endotracheal tube, for example. As is shown in FIG. 4B, the fluid conducting portion 52 includes a tube 53b, and the endotracheal tube 53a is inserted in the through tube 53b. The tube 53b is adequately long to extend beyond the laryngeal mask 14 toward the esophagus when in place in a patient and to extend out through the patient's mouth for easy access to insert the tube 53a or some other device therein to extend down to the patient's esophagus.

The endotracheal tube 53a and tube 53b may be made of plastic or of such other materials as endotracheal tubes typically are made or of some other suitable material. An inflation line 55 and air valve 56 may be used to expand the sealing balloon 54 to provide a seal with the wall of the esophagus 7 to prevent fluid flow along the outside of the tube 53a, although fluid may flow through the tube 53a. Applying air or other fluid to the sealing balloon 54 via the inflation line 55 and valve 56 after the endotracheal tube 52 has been inserted into the patient expands the balloon to form a seal; allowing that fluid to be withdrawn through the inflation line and air valve 56 allows the sealing balloon 54 to collapse to allow for relatively easy withdrawal of the endotracheal tube 52. Alternatively, the sealing balloon 54 may be another type of seal that does not require selective inflating and deflating, e.g., a resilient, deformable sealing balloon or other device that is suitably large to provide sealing function and still is sufficiently flexible and/or deformable to allow it to be inserted and withdrawn from the patient, e.g., esophagus.

The laryngeal mask 14 has a guide hole opening 57 through it to allow a portion 58 of the endotracheal tube 53a to extend therethrough. The guide hole opening 57 is so located in the laryngeal mask 14 as to position to the endotracheal tube 53a in position relative to the laryngeal mask such that the distal end 53d of the tube 53a would tend relatively easily to be guided for insertion into the esophagus 7 of a patient when the LMA 50 is properly inserted through the oral cavity (mouth) of the patient.

The opening 57 may be formed in a reinforced material portion of the inflatable member (cuff) 22 of the laryngeal mask 14 or the central support member 24 thereof. The opening 57 may be formed in a small tube-like member 57a that is mounted in the inflatable member 22 and/or in the central support member 24. The tube 53a may slide freely in the opening 57 or it may be fixed in that opening. In an exemplary embodiment, the tube 53a may slide relatively freely in the opening 57 when the inflatable member 22 of the laryngeal mask is uninflated, thereby to facilitate placing the distal end 53d of the tube 53a and the sealing balloon 54 in the esophagus 4. However, with the inflatable member 22 being inflated, it may tend to expand so as to cause the material at the opening 57 to engage the tube 53a relatively securely to retain it in position relative to the laryngeal mask 14. The inflatable member 22 may be inflated after it has been positioned in the oral cavity 3 of the patient so that the inflated walls of the inflatable member engage walls of the oral cavity to hold the laryngeal mask 14 in position in the oral cavity while also tending to hold the tube 53a in position. Thus, the portions 51, 52 of the LMA 50 would be held in relatively fixed position relative to the oral cavity and to the esophagus 7 and trachea 4.

As is illustrated in FIG. 4B, the tube 53b may be positioned relative to the fluid conducting portion 51 and the laryngeal mask 14 thereof in a manner similar to the manner described above for the endotracheal tube 53a. In this case the endotracheal tube 53a may be inserted through the tube 53b to the illustrated location in the esophagus to provide the functions described herein for the endotracheal tube.

Figures 5A, 5B:
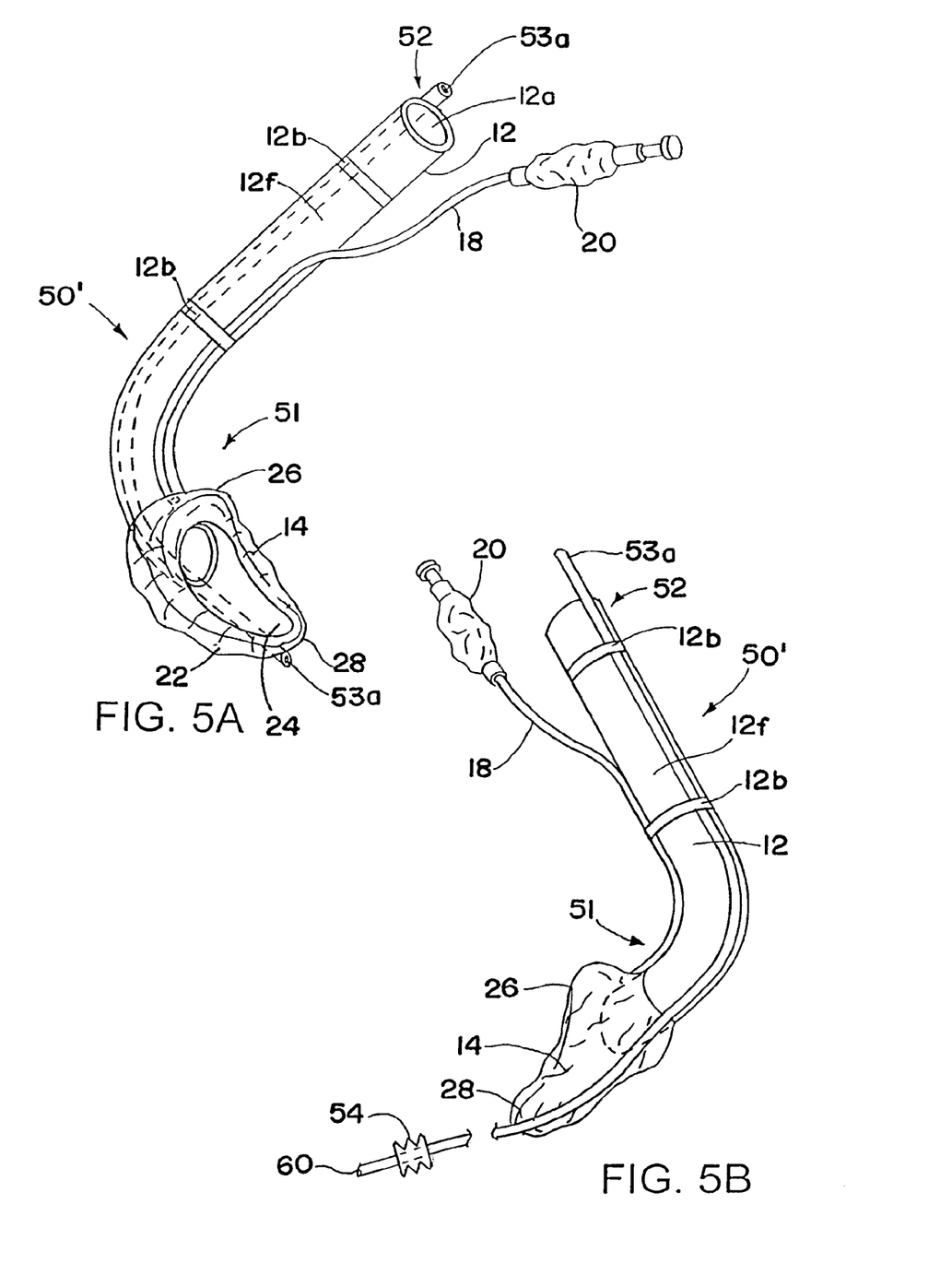
FIGS. 5A and 5B are front and rear perspective views of a laryngeal mask airway in accordance with an embodiment of the present invention including a passageway extending outside and held to the tube of the laryngeal mask.

Briefly referring to FIGS. 5A and 5B, another embodiment of LMA 50' is illustrated. The parts of the LMA 50' are similar to those described above with respect to FIGS. 3A, 3B, 3C, 4A and 4B, except that the endotracheal tube 53a of the fluid conducting portion 52 is attached to the exterior of the fluid conducting portion 51. As is seen in the drawings, the portion of the tube 53a that is parallel to and substantially coextensive with the tube 12 is attached, e.g., by adhesive material or by some other fastening mechanism, such as, for example, a band 12b, or a clamp, rivet or other device (not shown), to the exterior surface 12f of the tube 12. In the area where the tube 53a passes adjacent the inflatable member 22 and support portion 24 of the laryngeal mask 14 rather than through either one of them, the tube 53a may be attached to the laryngeal mask material or may have sufficient rigidity to follow the J-shape configuration of the tube 12 just upstream of and at the area of the laryngeal mask. In FIGS. 5A and 5B the endotracheal tube 53a does not have a separate inflation line for the sealing balloon 54; rather the sealing balloon may be somewhat normally expanded and adequately flexible to slide into position in the esophagus (or in the trachea) of a patient while making sealing engagement with the adjacent wall of the esophagus or trachea.

Figures 6A, 6B:
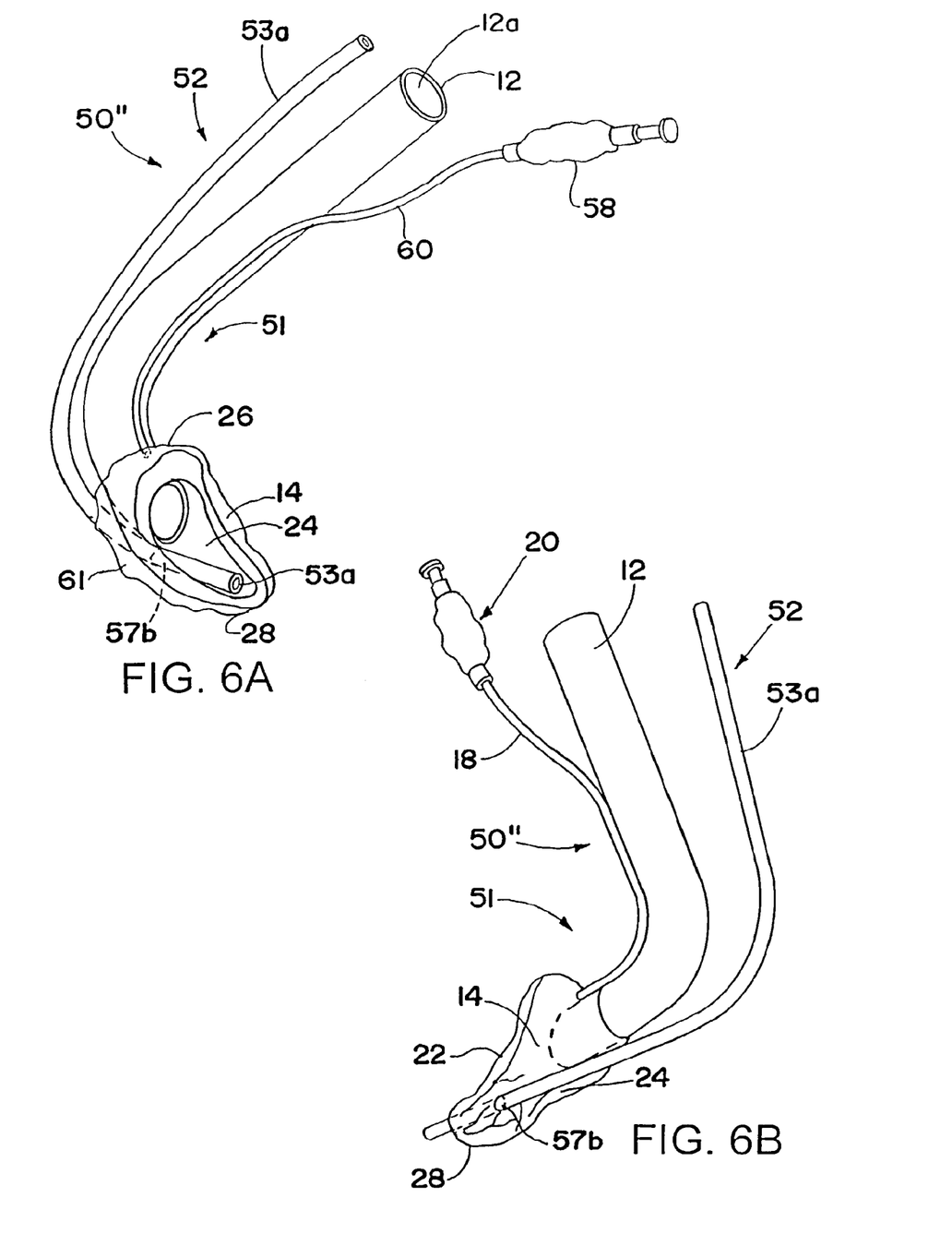
FIGS. 6A and 6B are front and rear perspective views of a laryngeal mask airway in accordance with an embodiment of the present invention including a passageway extending through a support portion of the laryngeal mask.

In FIGS. 6A and 6B, which are similar to FIGS. 4A and 4B, another LMA 50' is shown. An opening 57b is in the support portion 24 rather than in the inflatable member 22; and the tube 53a passes through such opening 57b. Although not shown in the drawing, if desired suitable reinforcement material, e.g., a separate tube section or thickened material that forms the support portion 24, may be provided at the area of the opening 57a to provide a suitable seal with the tube 53a and to avoid tearing of the support portion material on account of movement of the tube 53a relative to the support member.

Figure 7A:
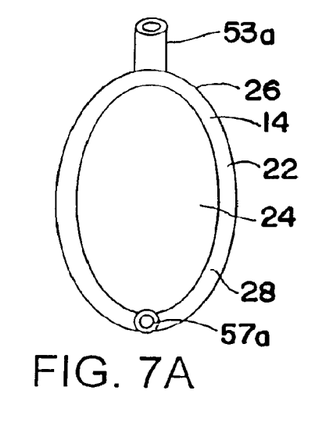
FIGS. 7A-7C are schematic front views of the laryngeal mask in accordance with respective embodiments of the present invention with the passageway through the inflatable member, outside the laryngeal mask, and through the support member, respectively.
Figure 7B:
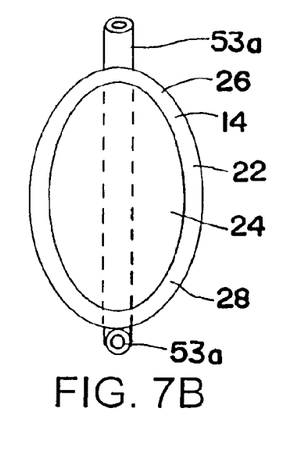
Figure 7C:
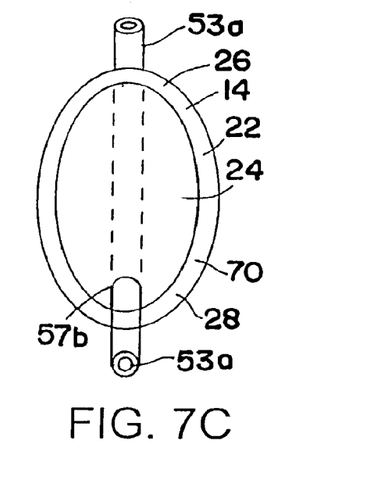

FIGS. 7A, 7B and 7C are schematic front plan views looking onto the laryngeal mask 14 to show exemplary locations at which the tube 53a extends outward therefrom, respectively, through the inflatable member 22 (FIG. 6A), outside the laryngeal mask and beneath (as illustrated) the inflatable member (FIG. 6B), and through the support member 24 (FIG. 6C).

The tubes 53a, 53b (sometimes referred to as passageways) may pass through the laryngeal mask 14 without interfering with the inflation or deflation of the laryngeal mask. One of ordinary skill in the art will readily appreciate that the tubes 53a, 53b may be secured above or below the central support member 12 and further that the tubes 53a, 53b may exit above or below the central support member 12. The location of the distal opening 60, 61 of the tubes 53a, 53b is positioned to provide a convenient pathway to the patient's esophagus.

The tube 53b may be made of a similar material as the tube 53a (e.g., plastic with sufficient strength and rigidity to keep the patient's teeth apart and prevent the patient from biting down and altering or damaging the tube). The tube 53b may also be made of a material more compliant or elastic than the material that the tube 12 is made (e.g., rubber, relatively soft or flexible plastic, etc.) so that the material will not interfere with insertion of the laryngeal mask airway 50.

Figure 8:
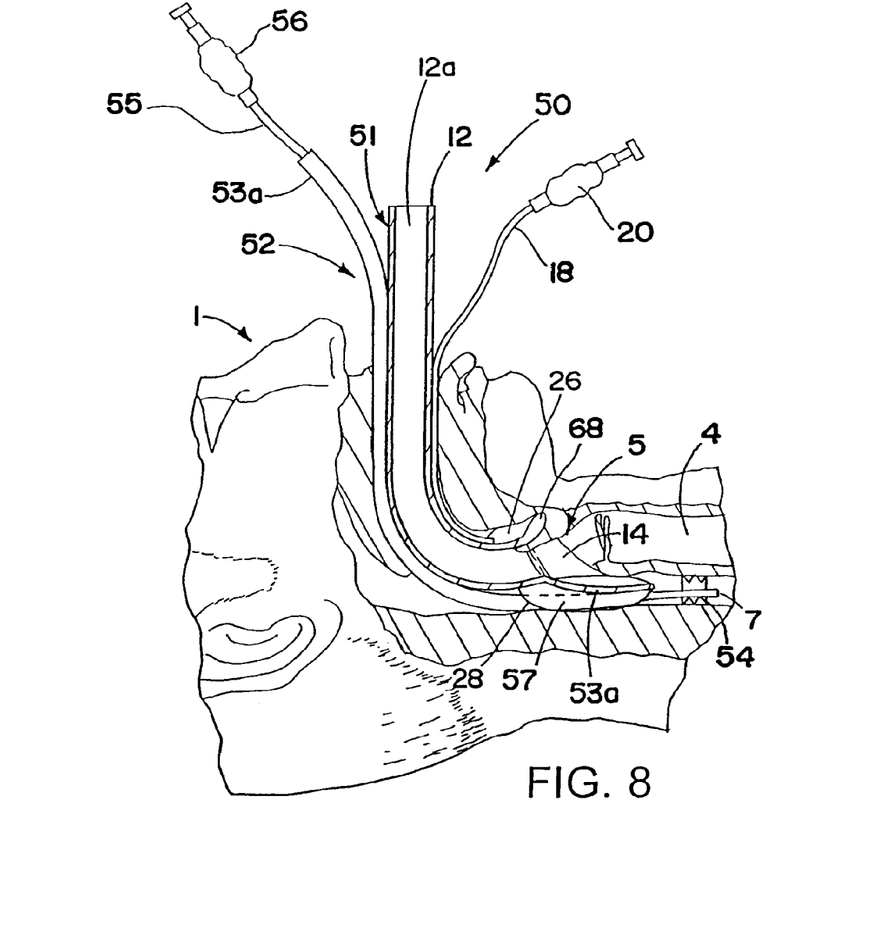
FIG. 8 is a cross-sectional view of a laryngeal mask airway in accordance with an embodiment of the present invention in a patient's airway after the laryngeal mask has been positioned and the endotracheal tube has been inserted in the esophagus.

Referring to FIG. 8 as well as to the other drawing figures, methods for using the laryngeal mask airway 50 of embodiments of the present invention will now be described. The curved distal portion of the tubular guide 12 is first inserted into the patient's mouth and laryngopharynx with the laryngeal mask 14 deflated. After the distal portion of the tubular guide 12 and the laryngeal mask 14 are appropriately positioned relative to the patient's laryngeal inlet 5, the laryngeal mask 14 is inflated via the inflation tube 18 and the air valve 20 to establish a seal around the patient's laryngeal inlet, as illustrated in FIG. 8. The lower portion 28 of the inflated laryngeal mask 14 substantially blocks the patient's esophagus. The upper portion 26 of the inflated laryngeal mask 14 substantially fills the patient's laryngopharynx adjacent to the laryngeal inlet 5. The laryngeal mask 14 thereby seals the distal opening of the tubular guide 12 in fluid communication with the patient's laryngeal inlet. The side portions of the laryngeal mask may pinch the sides of the patient's epiglottis, which also tends to lift the epiglottis from the laryngeal inlet, thereby clearing an airway to the patient's trachea 4. After the laryngeal mask 14 is properly positioned and inflated in the mouth of the patient, an instrumentality (e.g., an endotracheal tube 53a, an endoscope, a drainage tube, etc.) can be inserted into the esophagus 7 through passageway (tube) 53b (FIG. 4B, for example).

Alternatively, the tube 53b may be inserted through the guide hole 57 after the laryngeal mask 14 is in place in a patient; and thereafter another instrumentality can be inserted into the esophagus 7 through tube 53b.

As another alternative, the instrumentality, e.g., an endotracheal tube 53a, may be inserted through the guide hole after the laryngeal mask 14 has been placed in the patient; this may be difficult if the inflatable member 22 already has been inflated, but if it is not inflated it may be difficult to insert the instrumentality through the guide hole 57 due to the inflatable member 22 being somewhat flaccid.

Even another alternative is to have the instrumentality, e.g., endotracheal tube 53a, in position in the guide hole and extending generally in the manner illustrated in FIG. 8 and the other figures hereof, prior to placing the laryngeal mask 14 in the patient; and in this case the placing of the laryngeal mask 14 in the patient also would include guiding the distal end of such endotracheal tube 53a (or other instrumentality that is positioned by the guide hole 57) to the esophagus 7. The inflatable member 22 may be inflated after positioning the laryngeal mask 14 properly in the patient as described above.

After the instrumentality, e.g., endotracheal tube 53a, has been inserted into the esophagus a suitable distance, e.g., approximately three to four inches, so as to place the sealing balloon or cuff 54 in relation to the esophagus so that it can form a seal therewith, the sealing balloon is inflated via inflation tube 55 and air valve 56 from a suitable inflation source, e.g., an air pump or source of compressed air. In the present example, the cuff 54 is shaped to conform to the contours of the patient's esophagus.

Upon inflation of the sealing balloon or cuff 54, the patient's esophagus 7 is isolated from the inlet 5 to the trachea 4. The physician may then use the hollow tubular guide 12 and/or another instrumentality (e.g., an endotracheal tube, an endoscope, a drainage tube, etc.) (not shown) to provide air/oxygen to the patient via a ventilator/respirator (not shown) or perform other desired functions with the instrumentality.

By inserting the instrumentality 53a, for example, through the tube or passageway 53b and into the esophagus 7 and inflating the sealing balloon or cuff 54, any fluid regurgitated from the stomach may flow up through the instrumentality 53a and be removed outside the mouth of the patient through the instrumentality 53a. Therefore, any regurgitated material and/or fluid may be prevented from entering the lungs of the patient. Thus, the isolation of the stomach and esophagus is accomplished by both the instrumentality 53a and cuff 54 and by the inflated laryngeal mask 14, both of which block flow from the esophagus to the trachea. Meanwhile the patient may be ventilated via the tubular guide 12 without any interference with the passageway leading to the trachea for respiration and/or ventilation assistance.

Figure 9:
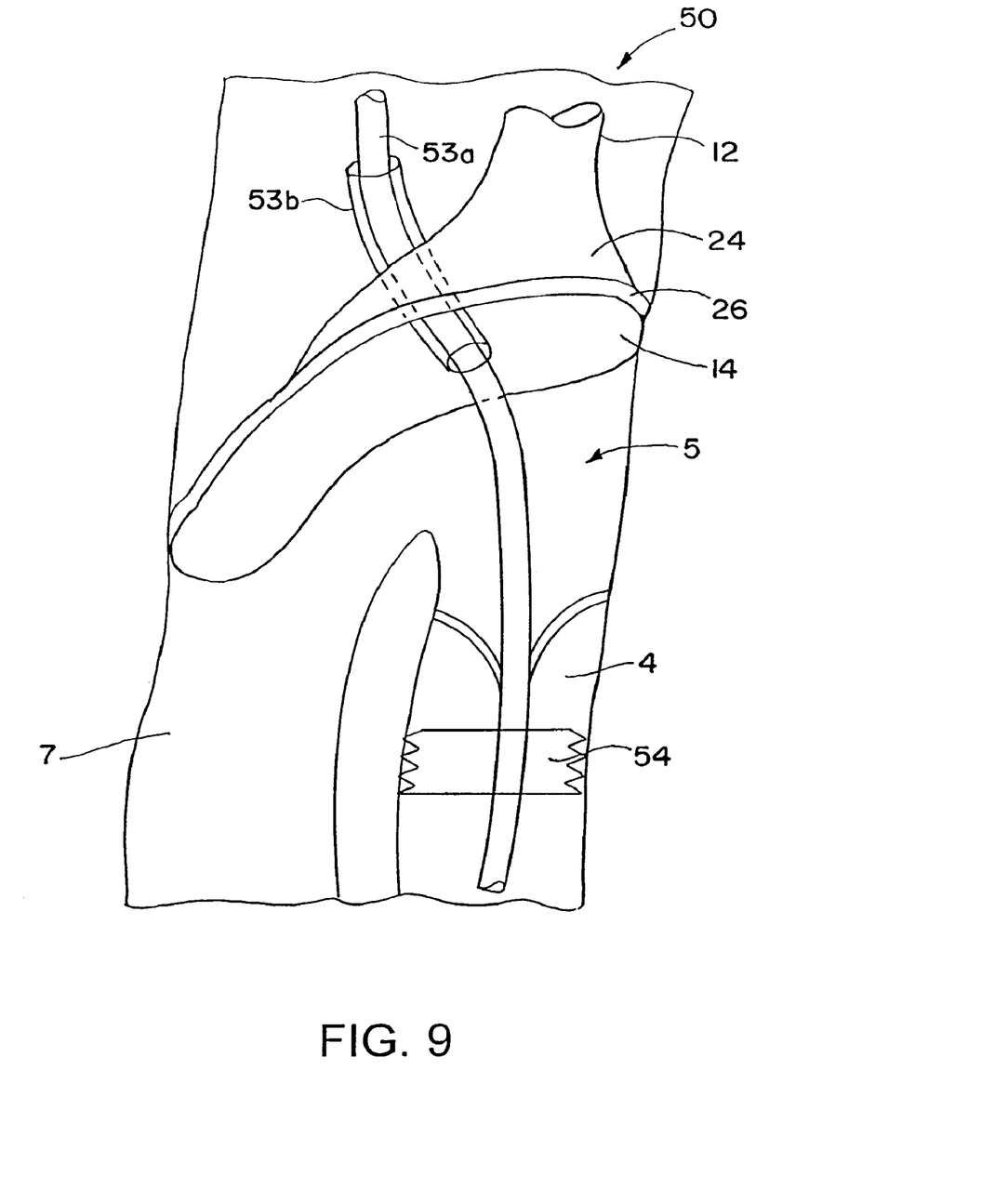
FIGS. 9 and 10 are schematic side elevation views showing a laryngeal mask airway in various orientations in the oral cavity of a patient.
Figure 10:
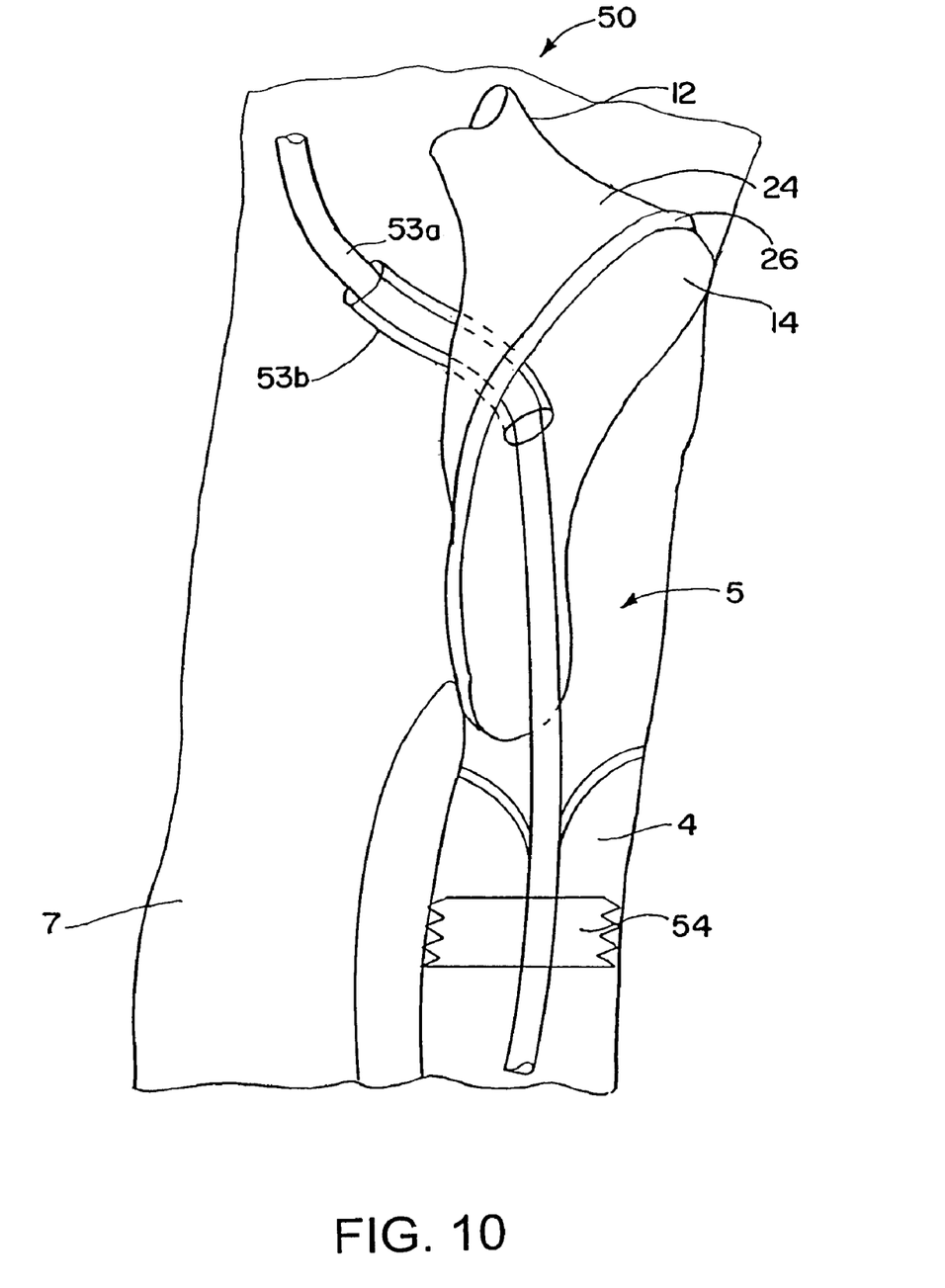

Alternatively, as is illustrated schematically in FIGS. 9 and 10 if instrumentality 53a, e.g., endotracheal tube, were inserted through the tube 53b into the trachea (instead of the esophagus), the cuff 54 may be inflated within the patient's trachea to block the flow of fluids and particulates into the lungs. An air and/or anesthesia mix can be directed through the instrumentality 53a to the lungs in this instance. As shown in FIG. 9 the laryngeal mask 14 may be positioned so that it does not seal the trachea 4 from the esophagus 7, but it is open to at least the esophagus to provide a path to the passageway 12a of the tubular guide 12. If the patient were to regurgitate, the fluid and particulates could be removed via the recessed area in the support portion 24 of the laryngeal mask 14 and withdrawn through the tubular guide 12 or another instrumentality that is in the tubular guide, e.g. a drainage tube in this particular instance. The proximal end of the drainage tube may in such case be connected to a suction device (not shown) to remove any undesirable fluids and particulates. As shown in FIG. 10 the laryngeal mask 14 may be positioned to block the trachea 4 but not the esophagus 7, while the instrumentality 53a, e.g., endotracheal tube, and cuff 54 are in the trachea. In such case the laryngeal mask 14 still may have part exposed to the esophagus 7 to provide a fluid path for regurgitant or the like to be suctioned out via the passageway 12a of tubular guide 12 or if need another suction tube may be inserted to remove regurgitant, etc.

By effectively isolating the patient's esophagus from the trachea, the laryngeal mask airway 50 overcomes many drawbacks of the conventional laryngeal mask airway and may be used in many situations to provide a patient with an air/anesthesia mix and avoids the possibility of regurgitation or other material from entering the patient's lungs.

It should be appreciated that the above described device and method provides for a laryngeal mask that can be used in many more instances than a conventional laryngeal mask. Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A laryngeal mask airway device comprising:
   a tubular guide including a distal portion and a proximal portion;
   a laryngeal mask attached to the distal portion of the tubular guide, wherein the laryngeal mask includes a recessed proximal portion and a distal portion;
   a first passageway extending from the proximal portion of the tubular guide to the recessed proximal portion of the laryngeal mask; and
   a second passageway extending through a distal portion of the laryngeal mask,
   wherein the first and second passageways are isolated from each other.

2. The laryngeal mask airway device of claim 1, wherein at least one of the first and second passageways are flexible.

3. The laryngeal mask airway device of claim 2, wherein at least a portion of an outer periphery associated with the first passageway and an outer periphery associated with the second passageway are connected to each other.

4. A laryngeal mask airway device comprising:
   a tubular guide including a distal portion and a proximal portion;
   a laryngeal mask attached to the distal portion of the tubular guide, wherein the laryngeal mask includes a recessed proximal portion and a distal portion;
   a first passageway extending from the proximal portion of the tubular guide to the recessed proximal portion of the laryngeal mask; and
   a second passageway extending through a distal portion of the laryngeal mask,
   wherein the first and second passageways are capable of receiving an endotracheal tube.

5. A laryngeal mask airway device comprising:
   a tubular guide including a distal portion and a proximal portion;
   a laryngeal mask attached to the distal portion of the tubular guide, wherein the laryngeal mask includes a recessed proximal portion and a distal portion;
   a first passageway extending from the proximal portion of the tubular guide to the recessed proximal portion of the laryngeal mask; and
   a second passageway extending through a distal portion of the laryngeal mask,
   wherein a diameter associated with the first passageway is larger than a diameter associated with the second passageway.

6. A laryngeal mask airway device comprising:
   a tubular guide including a distal portion and a proximal portion;
   a laryngeal mask attached to the distal portion of the tubular guide, wherein the laryngeal mask includes a recessed proximal portion and a distal portion;
   a first passageway extending from the proximal portion of the tubular guide to the recessed proximal portion of the laryngeal mask; and
   a second passageway extending through a distal portion of the laryngeal mask,
   wherein a diameter associated with the first passageway is smaller than a diameter associated with the second passageway.

7. A laryngeal mask airway device comprising:
   a tubular guide including a distal portion and a proximal portion;
   a laryngeal mask attached to the distal portion of the tubular guide, wherein the laryngeal mask further includes a support member;
   a first passageway extending from the proximal portion of the tubular guide to a position within the laryngeal mask located above the support member; and
   a second passageway extending generally along the tubular guide and extending through a distal portion of the laryngeal mask,
   wherein the first and second passageways are isolated from each other.

8. The laryngeal mask airway device of claim 7, wherein at least one of the first and second passageways are flexible.

9. The laryngeal mask airway device of claim 8, wherein at least a portion of an outer periphery of the first and second passageways are connected to each other.

10. A laryngeal mask airway device comprising:
    a tubular guide including a distal portion and a proximal portion;
    a laryngeal mask attached to the distal portion of the tubular guide, wherein the laryngeal mask further includes a support member;
    a first passageway extending from the proximal portion of the tubular guide to a position within the laryngeal mask located above the support member; and
    a second passageway extending generally along the tubular guide and extending through a distal portion of the laryngeal mask,
    wherein the first and second passageways are capable of receiving an endotracheal tube.

11. A laryngeal mask airway device comprising:
    a tubular guide including a distal portion and a proximal portion;
    a laryngeal mask attached to the distal portion of the tubular guide, wherein the laryngeal mask further includes a support member;
    a first passageway extending from the proximal portion of the tubular guide to a position within the laryngeal mask located above the support member; and
    a second passageway extending generally along the tubular guide and extending through a distal portion of the laryngeal mask,
    wherein one of the first passageway or second passageway is sized to receive a drainage tube and the other of the first passageway or the second passageway is sized to receive an endotracheal tube.

12. The laryngeal mask airway device of claim 11, wherein the first passageway is sized to receive an endotracheal tube and the second passageway is sized to receive a drainage tube.

13. A laryngeal mask airway device comprising:
    a tubular guide including a distal portion and a proximal portion;
    a laryngeal mask attached to the distal portion of the tubular guide, wherein the laryngeal mask further includes a support member;
    a first passageway extending from the proximal portion of the tubular guide to a position within the laryngeal mask located above the support member; and a second passageway extending generally along the tubular guide and extending through a distal portion of the laryngeal mask, wherein a diameter associated with the first passageway is larger than a diameter associated with the second passageway.

14. A laryngeal mask airway device comprising:

a tubular guide including a distal portion and a proximal portion;

a laryngeal mask attached to the distal portion of the tubular guide, wherein the laryngeal mask further includes a support member;

a first passageway extending from the proximal portion of the tubular guide to a position within the laryngeal mask located above the support member; and a second passageway extending generally along the tubular guide and extending through a distal portion of the laryngeal mask, wherein a diameter associated with the second passageway is larger than a diameter associated with the first passageway.

15. A laryngeal mask airway device comprising:

a tubular guide including a distal portion and a proximal portion;

a laryngeal mask attached to the distal portion of the tubular guide, wherein the laryngeal mask further includes a support member;

a first passageway extending from the proximal portion of the tubular guide to a position within the laryngeal mask located above the support member; and a second passageway extending generally along the tubular guide and extending through a distal portion of the laryngeal mask, wherein a diameter associated with the first passageway is smaller than a diameter associated with the second passageway.

16. The laryngeal mask airway device of claim 11, wherein the second passageway is sized to receive an endotracheal tube and the first passageway is sized to receive a drainage tube.

* * * * *